(12) United States Patent
Sugito et al.

(10) Patent No.: US 7,300,427 B2
(45) Date of Patent: Nov. 27, 2007

(54) DISPOSABLE WEARING ARTICLE

(75) Inventors: Tomoko Sugito, Kagawa-ken (JP);
Yoshio Ono, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 11/334,366

(22) Filed: Jan. 19, 2006

(65) Prior Publication Data
US 2006/0161126 A1 Jul. 20, 2006

(30) Foreign Application Priority Data
Jan. 20, 2005 (JP) ............... 2005-12505

(51) Int. Cl.
*A61F 13/15* (2006.01)
(52) U.S. Cl. ............ 604/387; 604/391; 604/386; 604/389; 604/385.25; 604/385.29; 604/385.27
(58) Field of Classification Search .......... 604/387, 604/386, 389, 385.29, 385.25, 385.27, 391
See application file for complete search history.

(56) References Cited

U.S. PATENT DOCUMENTS

| 6,149,639 | A | 11/2000 | Lundberg et al. | |
|---|---|---|---|---|
| 2003/0135190 | A1* | 7/2003 | Widlunc et al. | ............ 604/389 |
| 2004/0006327 | A1 | 1/2004 | Karami | |
| 2004/0236303 | A1* | 11/2004 | Igaue et al. | ............... 604/391 |
| 2005/0177126 | A1 | 8/2005 | Kurata | |

FOREIGN PATENT DOCUMENTS

| EP | 1166736 | 1/2002 |
|---|---|---|
| GB | 2267024 | * 11/1993 |
| JP | 3059224 | 3/1999 |
| WO | 95/30397 | 11/1995 |
| WO | 97/23180 | 7/1997 |
| WO | 9736566 | 10/1997 |
| WO | 00/37010 | 6/2000 |
| WO | 0113843 | 3/2001 |
| WO | 0113845 | 3/2001 |

* cited by examiner

Primary Examiner—Tatyana Zalukaeva
Assistant Examiner—Ginger T. Chapman
(74) Attorney, Agent, or Firm—Lowe, Hauptman, Ham & Berner LLP

(57) ABSTRACT

A disposable wearing article includes connector sheet strips used to connect front and rear waist regions of the article which respectively includes proximal sections and flap-like sections. The proximal sections are fixed to the rear waist region on its inner surface along zones immediately adjacent to transversely opposite side edges of the rear waist region and the flap-like sections extend from the respective zones to the inside of the article in a circumferential direction. The flap-like sections are formed with folding guide means facilitating the flap-like sections to be folded so that these flap-like sections may extend from the inside toward the outside of the article.

17 Claims, 7 Drawing Sheets

DISPOSABLE WEARING ARTICLE

RELATED APPLICATIONS

The present application is based on, and claims priority from, Japanese Application Number 2005-12505, filed Jan. 20, 2005, the disclosure of which is hereby incorporated by reference herein in its entirety.

BACKGROUND OF THE INVENTION

The present invention relates to a disposable wearing article adapted to be used in the form of, for example, a disposable diaper, a disposable diaper for incontinent patient, a disposable diaper cover or disposable training pants.

As one example of such disposable wearing articles, the disposable diaper having its front and rear waist regions adapted to be connected with each other in releasable and refastenable manner by means of sheet-like fasteners is well known. To be used with such disposable diaper of well known art, an example of such fasteners has one end as viewed in a transverse direction of the diaper is adapted to be permanently attached to any one of the front and rear waist regions in the vicinity of a side edge of this waist region. For example, Japanese Patent Publication No. 3096152 (PATENT DOCUMENT 1) discloses the invention relating to a disposable diaper 100 of this type as illustrated by FIGS. 6 and 7 of the accompanying drawings of this specification. The diaper 100 includes sheet-like fastening strips 106. In the case of this diaper 100 of prior art, transversely opposite side edges 103 of a front waist region 101 are put flat together with transversely opposite side edges 104 of a rear waist region 102, then proximal sections 107 of the respective fastening strips 106 having respective distal sections provided on inner surfaces thereof with anchoring layers 105 are put flat together with the transversely opposite side edges 103 of the front waist region 101 and these portions put flat together in this manner are integrally bonded together to form respective joints 108. The front waist region 101 is provided immediately inside the respective joints 108 with cutoff lines 109a along which the front waist region 101 may be separated from the rear waist region 102. When the diaper 100 can be put on the wearer's body in his or her standing position, the diaper 100 previously formed in the type of pants may be put on the wearer's body without cutting off the front waist region 101 from the rear waist region 102. In this case, it is unnecessary to utilize the fastening strips 106 and these fastening strips 106 may be left fastened to the front waist region 101 by means of the anchoring layers 105 to prevent the diaper 100 from getting out its proper position. When the diaper should be put on the wearer's body being in side lying position or lying face up, the front waist region 101 or the fastening strips 106 may be pulled to tear the diaper 100 along the cutoff lines 109a so that the transversely opposite side edges of the front waist region 101 may be separated from the transversely opposite side edges of the rear waist region 102 to obtain the open-type diaper shown by FIG. 7. After such open-type diaper has been appropriately placed on the wearer's body, the fastening strips 105 may be fastened to selected positions on the front waist region 101 by means of the respective anchoring layers 105.

In the case of this well known diaper 100 disclosed in PATENT DOCUMENT 1, the transversely opposite side edges 103 of the front waist region 101, the transversely opposite side edges 104 of the rear waist region 102 and the proximal sections 107 of the respective fastening strips 107 are put flat and bonded together to form the respective joints 108 while the distal sections of the respective fastening strips 106 carrying on the inner surfaces thereof the anchoring layers 105 extend inward from the respective joints 108 over the front waist region 101 as will be seen in FIG. 6. When it is desired to put such diaper 100 into the form of the open-type diaper, the fastening strips 106 must be turned around so that the respective distal sections carrying thereon the anchoring layers 105 extend outward from the respective joints 108 beyond the transversely opposite side edges 104 of the rear waist region 102 as seen in FIG. 7. However, in view of the manner in which the fastening strips 106 are bonded to the diaper 100 as illustrated by FIG. 6, these fastening strips 106 once having been turned around outward may easily restore the initial positions, i.e., it may be impossible for these fastening strips 106 to maintain the positions thereof illustrated by FIG. 7. To deal with such behavior of the fastening strips 106, if it becomes obvious, a mother intending to put the diaper 100 on the wearer's body must at least temporarily hold the fastening strips 106 to prevent these fastening strips 106 from restoring the initial positions thereof before she can actually put the diaper 100 on the wearer's body. Correspondingly, handling of the diaper 100 may be accompanied with more or less trouble.

SUMMARY OF THE INVENTION

In view of the problem as has been described above, it is a principal object of the present invention to provide a wearing article including a pair of fastening strips attached thereto so as to extend inward from transversely opposite side edges of the article and used to connect front and rear waist regions thereof with each other so improved that these fastening strips can be easily turned around so as to extend outward from the transversely opposite side edges of the article.

The object set forth above is achieved, according to the present invention, by an improvement in the disposable wearing article having a longitudinal direction and a transverse direction orthogonal to each other; the article comprising: a front waist region; a rear waist region; a crotch region; the regions respectively having pairs of side edges opposed to each other in the transverse direction so as to extend in the longitudinal direction and pairs of front and rear ends opposed to each other in the longitudinal direction so as to extend in the transverse direction; one of the front and rear waist regions being provided with connector sheet strips attached thereto in a vicinity of the associated one of the pairs of side edges so as to be fastened to the other waist region in a releasable manner.

The improvement according to the present invention is characterized by that the connector sheet strips respectively comprising proximal sections fixed to the one waist region in the vicinity of the associated pair of side edges on the surface destined to face the wearer's skin and flap-like sections extending inward from the proximal sections and provided on respective surfaces thereof opposed to the inner surface with fastening means adapted to cooperate with outer surface of the other waist region opposed to the inner surface of the one waist region wherein the flap-like sections are respectively formed with folding guide means extending along the proximal sections facilitating a direction in which the flap-like sections extend to be reversed so that the flap-like sections extend from the inside toward the outside as viewed in the transverse direction.

According to one preferred embodiment defined by Claim 2, the folding guide means are defined by fold lines formed on the flap-like sections in order to facilitate the flap-like sections to be turned around along the fold lines from the inside toward the outside as viewed in the transverse direction.

According to another preferred embodiment defined by Claim 3, the connector sheet strips contain any one of thermoplastic polymeric fiber and film made of thermoplastic polymer adapted to be deformed and to form the folding lines when pressurized under heating.

According to yet another preferred embodiment defined by Claim 4, one of two sections of the connector sheet strip contiguous to each other and extending in the transverse direction with interposition of the folding guide means constitutes the proximal section obtains a flexural rigidity in the transverse direction higher than that of the folding guide means in the transverse direction as a result of being fixed to the inner surface while the other section also obtains a flexural rigidity in the transverse direction higher than that of the folding guide means in the transverse direction as a result of being provided thereon with the fastening means and the folding guide means is defined by a region interposed between these two sections and having a relatively low flexural rigidity.

According to the invention defined by Claim 1, the flap-like sections of the respective connector sheet strips are formed with the folding guide means facilitating these flap-like sections to be turned around toward the outside of the wearing article in the transverse direction. Such unique arrangement effectively eliminates an apprehension that the flap-like sections might continue to extend toward the inside of the wearing article in the transverse direction and thereby make handling of the wearing article troublesome when the wearing article is put on the wearer's body in side lying position or face-up position.

According to the embodiment of the invention defined by Claim 2, the flap-like sections are formed with the fold lines so that these fold lines may function as the folding guide means.

According to the embodiment of the invention defined by Claim 3, any one of the thermoplastic polymeric fiber and the thermoplastic polymeric film contained in the flap-like sections maybe pressurized under heating to form the flap-like sections with the fold lines.

According to the embodiment of the invention defined by Claim 4, both the proximal section and the flap-like section provided with the fastening means in each of the respective connector sheet strips have the flexural rigidity in the transverse direction higher than the flexural rigidity in the transverse direction of the region interposed between these two sections so that this region having the relatively low flexural rigidity may function as the folding guide means.

DETAILED DESCRIPTION OF THE PREFERRED EMBODIMENTS

Details of the disposable wearing article according to the present invention will be fully understood from the description given hereunder in reference with the accompanying drawings illustrating disposable diapers as typical embodiment of the present invention.

Figure 1:
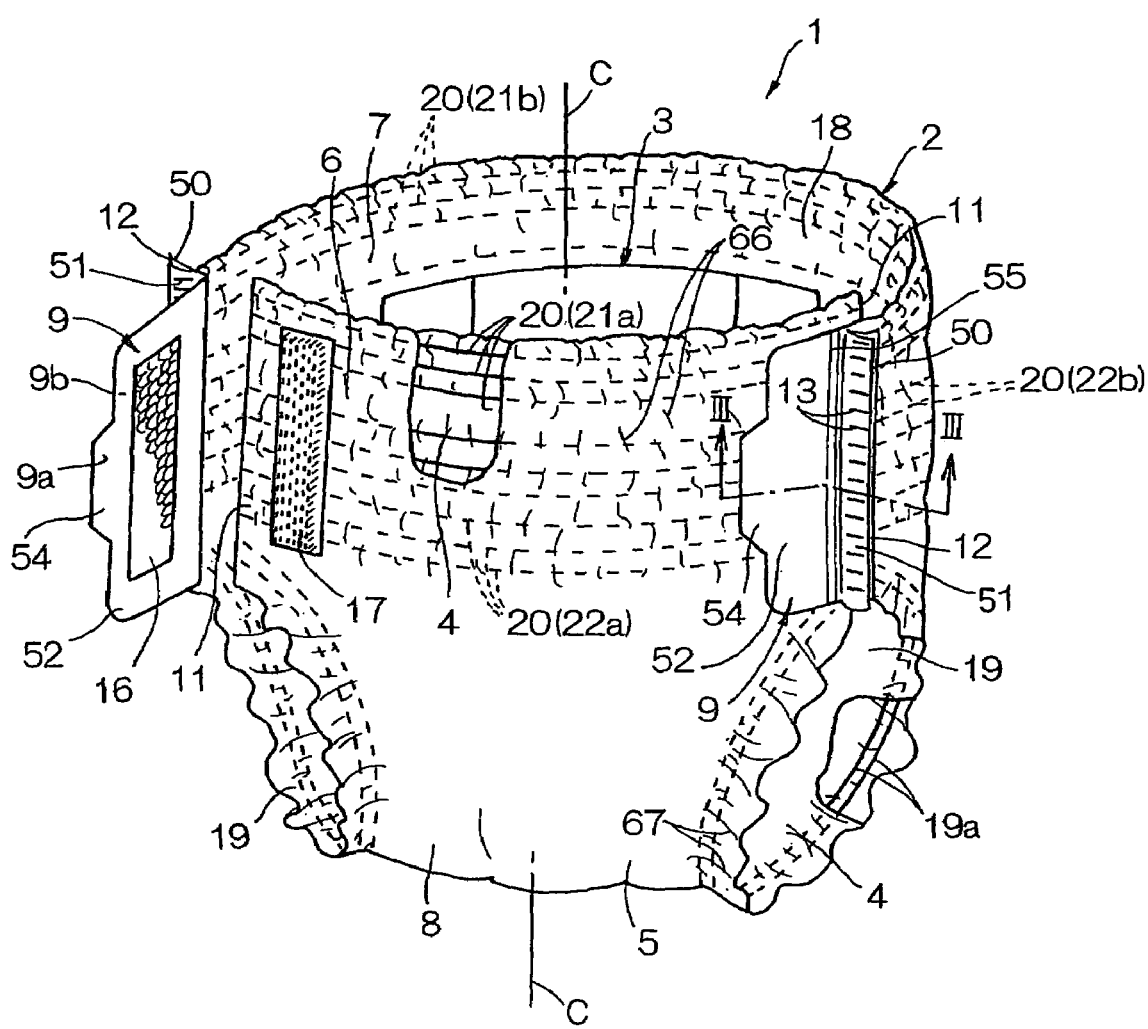
FIG. 1 is a partially cutaway perspective view showing a disposable diaper as a typical embodiment of the present invention with front and rear waist regions partially connected with each other.

FIG. 1 is a partially cutaway perspective view showing a disposable diaper 1 as put on the wearer's body. This disposable diaper 1 is suitable for baby and generally comprises a chassis 2 and a bodily fluid absorbent panel 3. The chassis 2 has a crotch region 8, a front waist region 6 defined in front of the crotch region 8 and a rear waist region 7 defined behind the crotch region 8. These regions 6, 7, 8 are respectively formed by a first sheet, i.e., an outer sheet 5 facing clothes (not shown) of the diaper wearer and a second sheet, i.e., an inner sheet 4 lying on the opposite side of the outer sheet 5 and facing the wearer's skin (not shown). In zones 50 respectively extending in the vicinity of transversely opposite side edges 12 of the rear waist region 7, the inner sheet 4 is out of contact with the wearer's skin Connector sheet strips 9 each comprising a third sheet prepared separately of the inner and outer sheets 4, 5 are put flat together with the respective zones 50 and bonded thereto at a plurality of bonding spots arranged along these zones 50 intermittently in a vertical direction as viewed in FIG. 1. Each of the connector sheet strips 9 is relatively long in the vertical direction as viewed in FIG. 1 and has inner and outer surfaces 9a, 9b. A loop member 16 constituting a mechanical fastener widely known in various trade names such as Magic Tape is attached to the inner surface 9a using appropriate adhesive or welding technique. The front waist region 6 is provided in the vicinity of transversely opposite side edges 11 with a hook member 17 constituting the mechanical fastener. Specifically, the hook member 17 is attached to the outer sheet 5 using appropriate adhesive or welding technique. In this way, the loop members 16 cooperate with the hook members 17 to function as fastening means so that the front waist region 6 and the rear waist region 7 may be connected with each other in releasable manner by means of the connector sheet strips 9 as these loop and hook members 16, 17 are placed upon each other. It should be noted here that FIG. 1 shows the front and rear waist regions 6, 7 connected with each other on the right hand but still not connected with each other on the left hand. Upon complete connection of the front and rear waist regions 6, 7 with each other, the diaper 1 is formed with a waist-hole 18 and a pair of leg-holes 19.

Each of the connector sheet strips 9 comprises a proximal section 51 fixed to the inner surface of the rear waist region 7 at the associated zone 50 thereof and a deformable flap-like section 52 extending from the proximal section 51 toward a center line C-C bisecting a width of the front waist region 6. With respect to the connector sheet strip 9 on the right hand in FIG. 1, the proximal section 51 bonded integrally to the associated zone 50 projects outward from the diaper 1 and the flap-like section 52 extends inward from the proximal section 51 in the transverse direction of the front waist region 6. A distal end of the flap-like section 52 defines a finger-grip 54. The flap-like section 52 is further formed with folding guide means 55 extending along the proximal section 51 in the vertical direction as viewed in FIG. 1. On the left hand in FIG. 1, the flap-like section 52 is illustrated 5 as has been folded along the folding guide means 55.

The diaper 1 further includes a plurality of waist elastic members 20 extending in a circumferential direction of the waist-hole 18 and a plurality of leg elastic members 19a extending in a circumferential direction of the respective leg-holes 19. Contraction of these elastic members 20, 19a causes the chassis 2 to form gathers 66, 67 extending in a direction orthogonal to these elastic members 20, 19a, respectively, and repetitively undulating along these elastic members 20, 19a, respectively.

Figure 2:
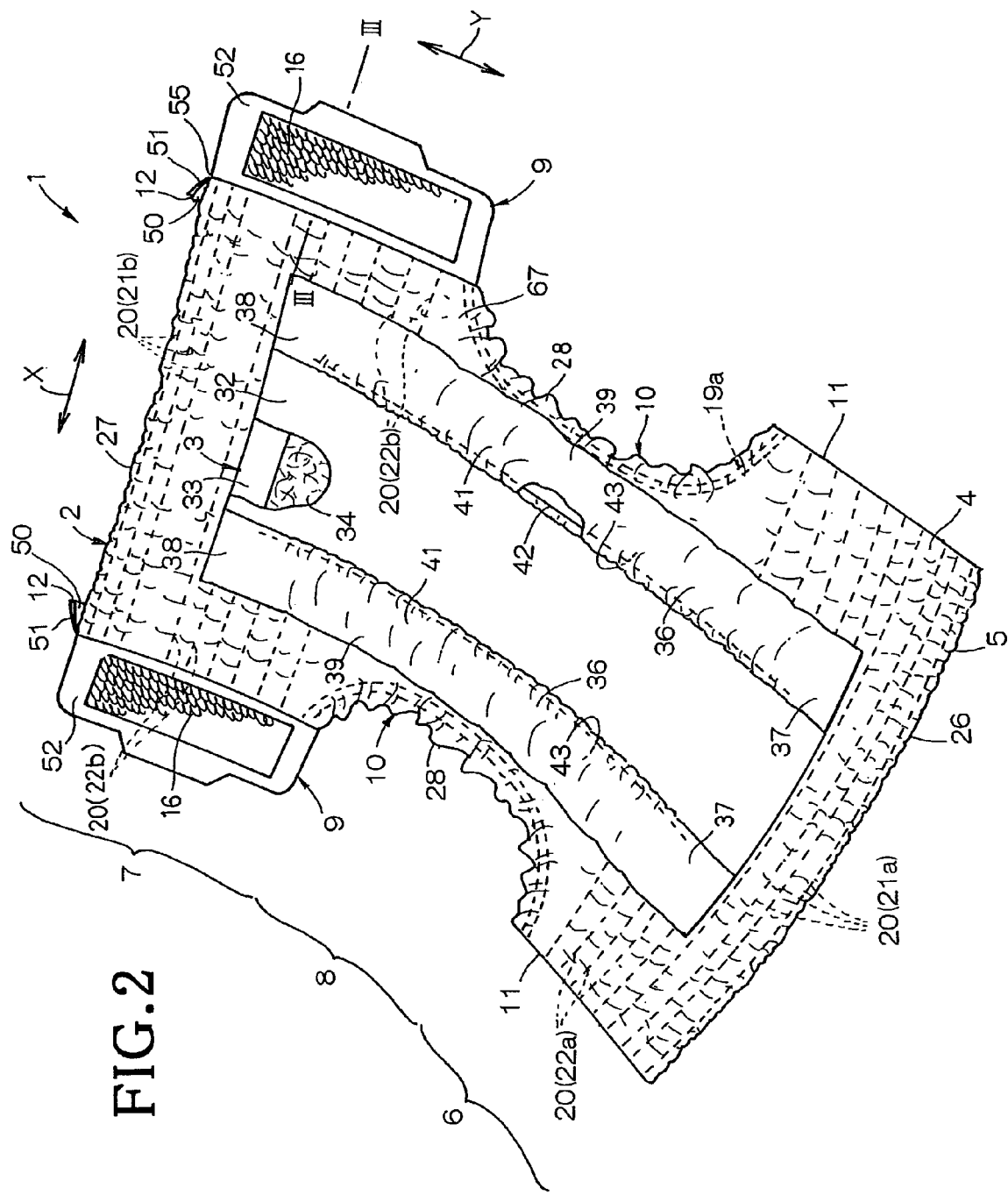
FIG. 2 is a partially cutaway perspective view showing the disposable diaper developed in a transverse direction as well as in a longitudinal direction.

FIG. 2 is a partially cutaway perspective view showing the diaper 1 with the front and rear waist regions 6, 7 disconnected from each other and developed in the transverse direction indicated by the double-headed arrow X as well as in the longitudinal direction indicated by a double-headed arrow Y which is orthogonal to the direction of the double-headed arrow X insomuch as the gathers 66, 67 do not completely disappear. With respect to the connector sheet strips 9, the respective flap-like sections 52 are illustrated in FIG. 2 as have been folded along the respective folding guide means 55 so as to extend outward in the transverse direction X of the diaper 1. The direction X corresponds also to a direction of a waist line. As will be apparent in FIG. 2, the chassis 2 has a pair of side edges 10 opposed to each other in the transverse direction X and extending in the longitudinal direction. The opposite side edges 10 includes a front pair of edges 11 defined by transversely opposite side edges of the front waist region 6 and a rear pair of transversely opposite side edges 12 defined by transversely opposite side edges of the rear waist region 7. A width between the front pair of transversely opposite side edges 11 is narrower than a width between the rear pair of transversely opposite side edges 12. Of the transversely opposite side edges 10, a central pair of transversely opposite side edges 28 defined by transversely opposite side edges of the crotch region 8 curve from the outside to the inside of the chassis 2 so as to describe circular arcs. The front and rear waist regions 6, 7 respectively have front and rear ends 26, 27 opposed to each other in the longitudinal direction Y and extending in the transverse direction X. These front and rear ends 26, 27 define together a peripheral edge of the waist-hole 18 shown by FIG. 1. The waist elastic members 20 attached in stretched state to the chassis 2 so as to extend along the front and rear ends 26, 27. The waist elastic members 20 comprise at least a single first elastic member 21a for the front waist region 6 extending in stretched state between the front pair of side edges 11, 11 and at least a single first elastic member 21b for the rear waist region 7 extending in stretched state between the rear pair of rear side edges. The waist elastic members 20 further comprise a plurality of second elastic members 22a for the front waist region 6 and a plurality of second elastic members 22b for the rear waist region 7 both pairs laid below the respective first elastic members 21a, 21b and above the central pair of side edges 28 of the crotch region 8 so as to extend in stretched state between the front pair of side edges 11, 11 and between the rear pair of side edges 12, 12, respectively. In a preferred diaper 1, the respective first elastic members 21a, 21b having a stretch stress higher than that of the respective second elastic members 22a, 22b in order to ensure that the respective first elastic members 21a, 21b are held in contact with the wearer's waist more tightly than the respective second elastic members 22a, 22b are. It is possible for the diaper 1 to use elastic members exhibiting an identical stretch stress as the respective first elastic members 21a, 21b as well as the respective second elastic members 22a, 22b or to use elastic members exhibiting stretch stresses different from each other as the respective first elastic members 21a, 21b or to use elastic members exhibiting stretch stresses different from each other as the respective second elastic members 22a, 22b. It is also possible for the diaper 1 to dispense with the second elastic members 22a and/or the second elastic members 22b. The leg elastic members 19a are attached in stretched state to the chassis 2 along the central pair of side edges 28 of the crotch region 8. These waist elastic members 20 and leg elastic members 19a are sandwiched between the inner and outer sheets 4, 5 and intermittently bonded to at least one, preferably to both of these inner and outer sheets 4, 5. The connector sheet strips 9 have the proximal sections 51 fixed to the zones 50 defined immediately inside the rear pair of side edges 12 and the flap-like sections 52 extending from the inside to the outside of the diaper 1 as viewed in the transverse direction X.

The bodily fluid absorbent panel 3 shown by FIG. 2 comprises a liquid-pervious topsheet 32, a liquid-impervious backsheet 33 and a bodily fluid absorbent core 34 sandwiched between these two sheets 32, 33. The top- and backsheets 32, 33 have portions extending outward beyond a peripheral edge of the core 34, these portions being put flat and bonded together using appropriate adhesive or welding technique. Such bodily fluid absorbent panel 3 is provided along transversely opposites with a pair of leak-proof barriers 36 preferably made of liquid-impervious sheets. The sheet material forming each of the leak-proof barriers 36 is bonded to the topsheet 32 at front and rear end sections 37, 38 and along an outer side edge 39 but left free from the topsheet 32 so far as an inner side edge 41 is concerned. To this inner side edge 41, an elastic member 42 extending in the longitudinal direction Y is attached in stretched state. The leak-proof barriers 36 constructed in such manner effectively form a pair of pockets 43 adapted to receive bodily fluid moving on the topsheet 32 in the transverse direction X. The backsheet 33 of the bodily fluid absorbent panel 3 is bonded to the inner sheet 4 of the chassis 2 by means of hot melt adhesive (not shown).

In the case of such diaper 1, both the inner sheet 4 and the outer sheet 5 are formed by nonwoven fabric, film or composite sheet consisting of these nonwoven fabric and film laminated one upon another, in any case, preferably containing therein thermoplastic polymer as essential ingredient. The topsheet 32 of the bodily fluid absorbent panel 3 has a basis weight of 10 to 30 $g/m^2$ and is formed by nonwoven fabric, perforated film or the like made of thermoplastic polymer. The backsheet 33 is formed by film, nonwoven fabric, composite sheet consisting of these film and nonwoven fabric laminated one upon another, or the like. The core 34 is formed by fluff pulp, a mixture of fluff pulp and super-absorbent polymer particles, or the like, in any case, compressed to a desired thickness and preferably wrapped with sheet material having high liquid-permeability and high liquid-diffusivity such as tissue paper. The connector sheet strip 9 is formed by nonwoven fabric or film, composite sheet consisting of these nonwoven fabric and film laminated one upon another, or the like, in any case, preferably containing therein thermoplastic polymer as essential ingredient. A preferred connector sheet strip 9 has a basis weight in a range of 15 to 200 $g/m^2$.

Figure 3:
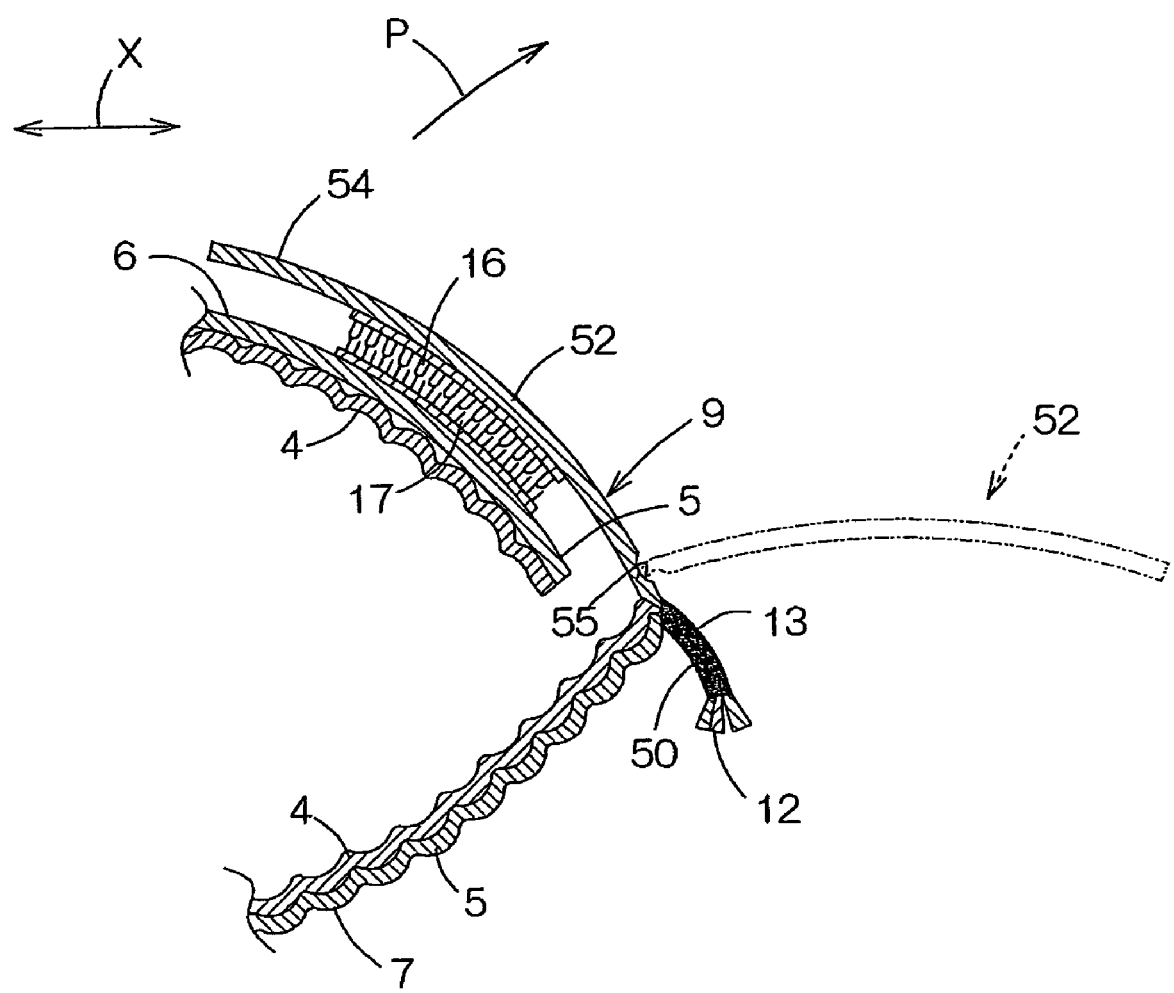
FIG. 3 is a sectional view taken along a line III-III in FIG. 1.

FIG. 3 is a sectional view taken along a line III-III in FIG. 1 wherein the line III-III extends across one of the zones 50 including the bonding spots 13 in parallel to the second elastic members 22a as will be seen in FIG. 1. Preferred bonding spots 13 are formed by thermoplastic polymer contained in any one of the inner sheet 4, the outer sheet 5 and the connector sheet strip 9 as these three sheet materials 4, 5 and 9 are heated under a pressure. More specifically, during this process, the thermoplastic polymer is molten and then solidified to weld these three sheet materials. In this way, the film-like bonding spots 13 are formed. Alternatively, the bonding spots 13 may be formed also by bonding the inner sheet 4, the outer sheet 5 and the connector sheet strip 9 together, for example, using hot melt adhesive.

The connector sheet strip 9 may be pulled in a direction indicated by an arrow P with the finger-grip 54 held by the fingers to disengage the loop member 16 of the flap-like section 52 from the hook member 17 of the front waist region 6 and thereby to disconnect the rear waist region 7 from the front waist region 6. In FIG. 3, the flap-like sections 52 extending inward from the zones 50 of the rear waist region 7 in the transverse direction are formed with the folding guide means 55 so that the flap-like sections 52 can be reversed, preferably by itself, from the inside toward the outside of the diaper 1 in the transverse direction. These folding guide means 55 ensure that, upon disengagement of the loop member 16 from the hook member 17, the flap-like sections 52 can be folded outward in the transverse direction X along these folding guide means 55 to the positions indicated by imaginary lines. These positions correspond to the positions of the flap-like sections 52 shown by FIG. 2. These folding guide means 55 along which the flap-like sections 52 are to be folded are permanently serve as folding means for the flap-like sections 52. In the case of the connector sheet strips 9 formed by nonwoven fabric made of thermoplastic polymeric fiber, film made of thermoplastic polymer, or the like, the sheet strips 9 may be folded and then cooled to obtain these folding guide means 55.

When the diaper 1 of FIG. 2 is put on a baby in side lying position or face-up position with the inner sheet 4 facing the wearer's skin, the flap-like sections 52 of this diaper 1 can be easily or by itself turned around outward in the transverse direction of the diaper 1 under the effect of the folding guide means 55 as illustrated by FIGS. 2 and 3. Compared to the case in which the flap-like sections 52 continue to extend in the transverse direction toward the inside of the diaper 1, the finger-grips 54 of the respective flap-like sections 52 can be easily caught by the fingers.

Figure 4:
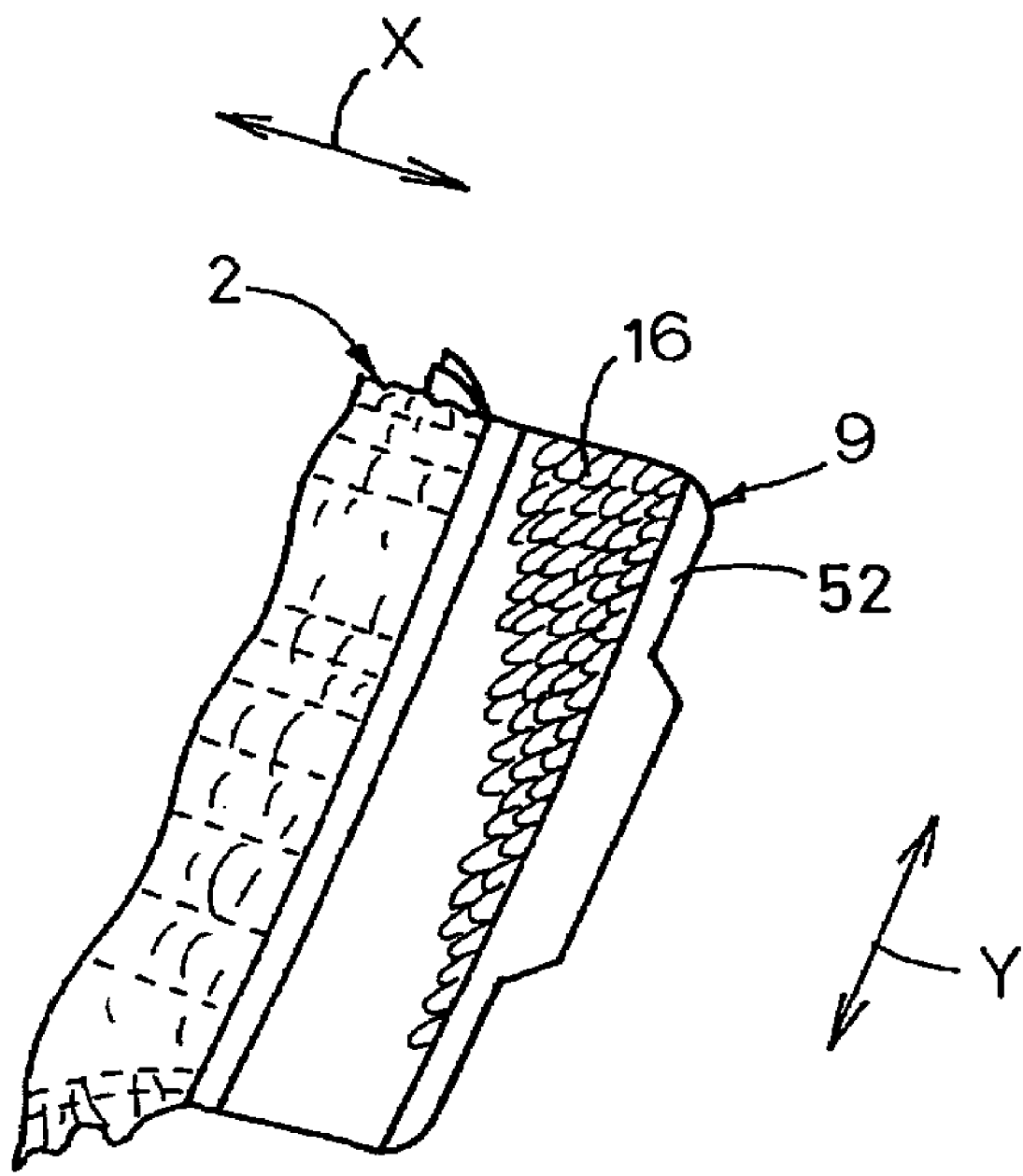
FIG. 4 is a fragmentary view of one preferred embodiment of the diaper according to the present invention.

FIG. 4 is a fragmentary view of one preferred embodiment of the diaper 1 according to the present invention. In this embodiment, each of the flap-like sections 52 is dimensioned identically to the flap-like section 52 in the embodiment shown by FIG. 2 and provided with the loop member 16 extending on the entire area of the flap-like section 52. Compared to the connector sheet strip 9 shown by FIG. 2, in which the loop member 16 has its dimension as measured in the longitudinal direction Y smaller than the dimension of the flap-like section 52, the flap-like section 52 of this embodiment has the high rigidity over the correspondingly larger extent. Correspondingly, a weight of the flap-like section 52 increases and thereby more effectively facilitates the flap-like section 52 to be reversed toward the outside of the diaper 1 in the transverse direction.

Figure 5:
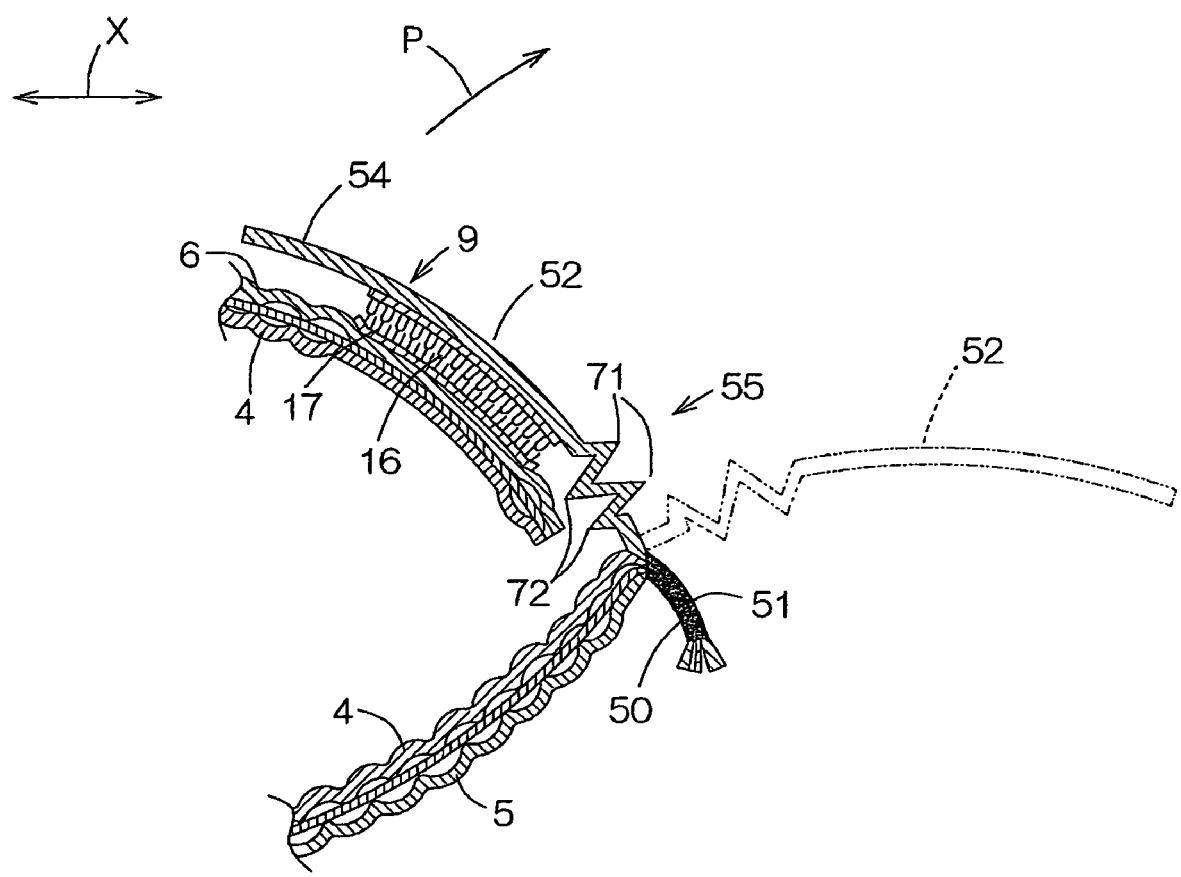
FIG. 5 is a view similar to FIG. 3, showing another preferred embodiment of the diaper according to the present invention.
Figure 6:
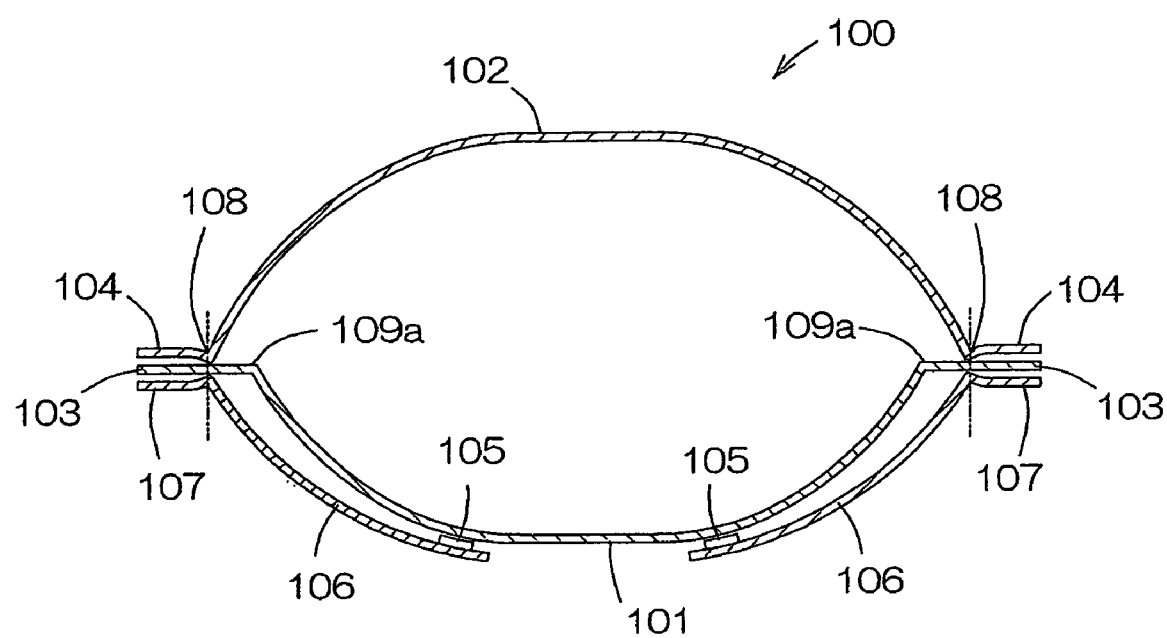
FIG. 6 is a schematic sectional view showing one example of the well known diapers.
Figure 7:
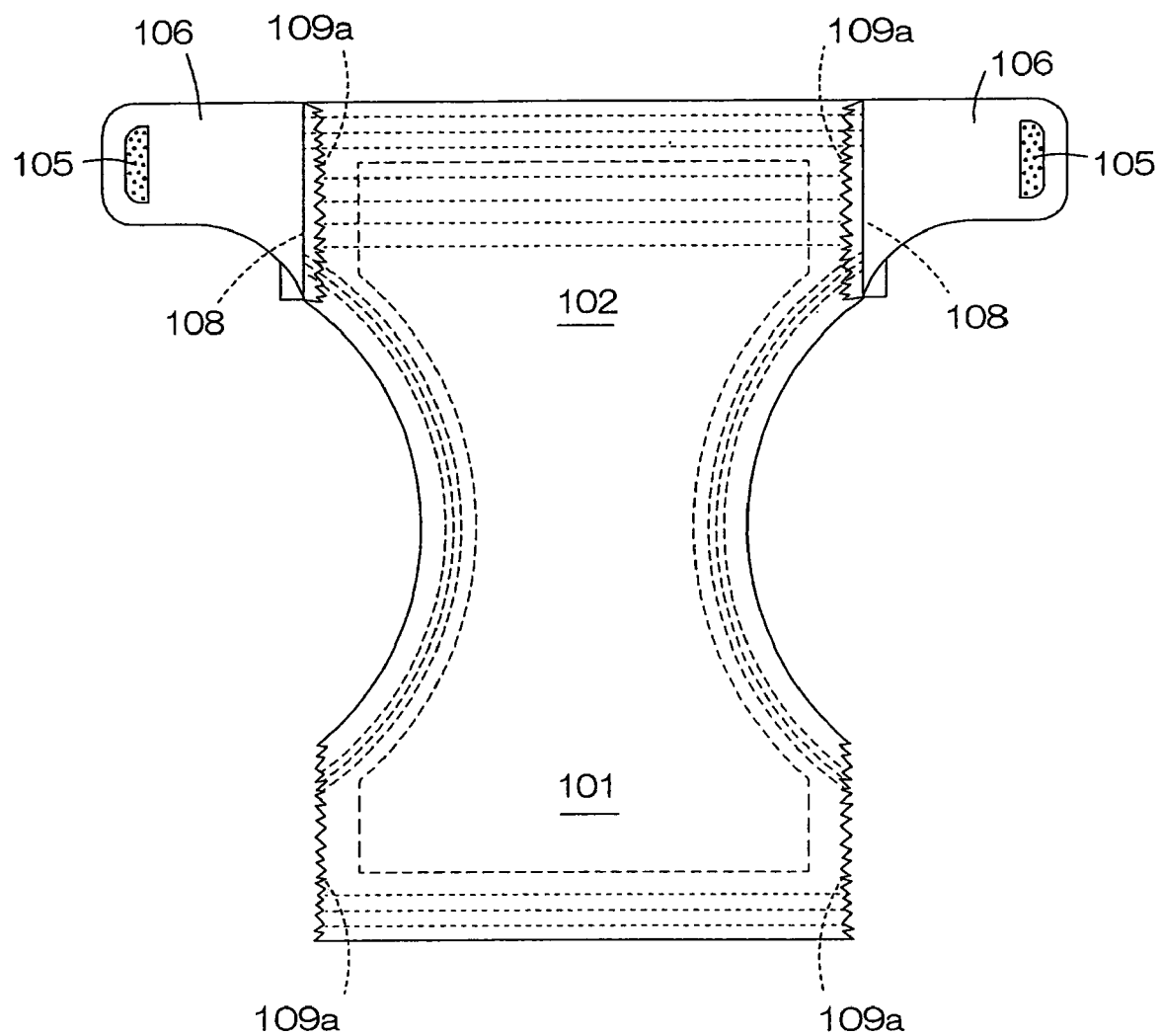
FIG. 7 is a developed plan view showing the well known diaper.

FIG. 5 is a view similar to FIG. 3, showing another embodiment of the invention. Each of the flap-like sections 52 in the respective connector sheet strips 9 according to this embodiment has folds comprising alternating crest 71 and trough 72 extending in parallel to each other in the vertical direction of the diaper 1 as viewed in FIG. 1 and serving as the folding guide means 55. One of two sections of the connector sheet strip 9 extending in the transverse direction with interposition of the folding guide means 55 constitutes the proximal section 51 and obtains a flexural rigidity in the transverse direction higher than that of the folding guide means in the same direction as a result of being fixed to the inner surface while the other section also obtains a flexural rigidity in the transverse direction higher than that of the folding guide means in the same direction as a result of being provided thereon with the fastening means and the folding guide means is defined by a region interposed between these two sections and having a relatively low flexural rigidity. This connector sheet strip 9 has the proximal section 51 lying on one side with respect to the folding guide means 55 as viewed in the transverse direction and this proximal section 51 obtains a high rigidity as a result of being bonded to the zone 50 immediately adjacent to the side edge of the diaper 1. The flap-like section of the connector sheet strip 9 lying on the other side with respect to the folding guide means 55 is provided thereon with the loop member 16 and exhibits a high rigidity in its area carrying the loop member 16. Compared to the proximal section 51 and the section carrying the loop member 16, a flexural rigidity of the folding guide means 55 interposed between these two sections has a relatively low rigidity as measured in the transverse direction X because of the alternating crest 71 and trough 72. Such uniquely differentiated of the rigidity facilitates the flap-like section 52 to be folded. Specifically, after the loop member 16 has been disengaged from the hook member 17 by pulling the connector sheet strip in the direction P with the finger-grip 54 held by the fingers, the flap-like section 52 can be easily turned around with the finger-grip 54 continuously held by the fingers to the position indicated by the imaginary lines. In the case of this diaper 1, even if it can not be expected for the flap-like section 52 to be turned around by itself toward the outside of the diaper 1, the flap-like section 52 can be easily turned around with the finger-grip 54 by the fingers. Similarly to the diaper 1 of FIG. 2, the diaper 1 can be smoothly put on the wearer's body without any troublesome handling.

Without departing from the scope of the invention, it is possible to attach the connector sheet strips 9 not to the rear waist region 7 but to the front waist region 6. It is also possible without departing from the scope of the invention to attach the loop member 16 to the front waist region 6 and to attach the hook members 17 to the associated connector sheet strip 9 vice versa with respect to the illustrated embodiment. It is further possible without departing from the scope of the invention to provide on the inner surfaces 9a of the respective flap-like sections 52 with pressure-sensitive adhesive layers serving as fastening means to the front waist region 6 and to provide the outer sheet 5 of the front waist region 6 with a target zone onto which those pressure-sensitive adhesive layers can be releasably anchored.

While the diaper 1 for baby has been described in reference with the accompanying drawings, the present invention may be implemented also in the various forms, for example, of disposable diaper for adult, disposable diaper for incontinent patient and disposable diaper comprising the bodily fluid absorbent core 34, instead of the bodily fluid absorbent panel 3, sandwiched between the liquid-pervious inner sheet 4 and the liquid-impervious outer sheet 5. Furthermore, the present invention may be implemented in the form of training pants, diaper cover or wearing article used to hold a urine retention pad both without being provided with the bodily fluid absorbent panel 3, or the like.

The present invention makes it possible to manufacture the disposable wearing article requiring no troublesome handling to put it on the wearing body.

The entire discloses of Japanese Patent Application No. 2005-12505 filed on Jan. 20, 2005 including specification, drawings and abstract are herein incorporated by reference in its entirety.

What is claimed is:

1. A disposable wearing article having a longitudinal direction and a transverse direction orthogonal to each other, said article comprising:
   a front waist region;
   a rear waist region;
   a crotch region;
   each of said regions having a pair of side edges opposed to each other in said transverse direction, and opposite inner and outer surfaces, the inner surface being adapted to face a wearer's skin in use and the outer surface being adapted to face away from the wearer's skin in use; and
   connector sheet strips attached to one of said front and rear waist regions in a vicinity of the associated side edges;
   each of said connector sheet strips respectively comprising:
   a proximal section fixed to the inner surface of said one waist region in the vicinity of one of said associated side edges;
   a flap section moveable between a first position where said flap section extends in the transverse direction inward from said proximal section and a second position where said flap section extends in the transverse direction outward from said proximal section, said flap section having a surface that is opposed to said inner surface of said one waist region when the flap section is in the first position;
   a fastening element provided on said surface of said flap section and releasably engageable with the outer surface of the other waist region; and
   a folding guide between said flap section and said proximal section, said folding guide extending along said proximal section to facilitate unfolding of said flap section from the first position to the second position;
   wherein said folding guide is spaced in the transverse direction from bonding sites where the proximal section is bonded to the respective side edge of said one waist region.

2. The wearing article defined by claim 1, wherein said folding guide comprises a folding line of reduced thickness formed in the respective connector sheet strip.

3. The wearing article defined by claim 2, wherein said connector sheet strips contain thermoplastic polymer deformable under pressure and heat to form said folding lines.

4. The wearing article defined by claim 1, wherein
   said proximal section has a flexural rigidity in said transverse direction higher than that of said folding guide as a result of being fixed to said inner surface; and
   said flap section has a flexural rigidity in said transverse direction higher than that of said folding guide as a result of being provided thereon with said fastening element.

5. The wearing article defined by claim 1, wherein said folding guide comprises multiple alternating crests and troughs.

6. The wearing article defined by claim 5, wherein a distance between one of the crests and an adjacent one of the troughs, as measured in a thickness direction of the respective connector sheet strip, is greater than a thickness of the respective connector sheet strip outside said folding guide.

7. The wearing article defined by claim 5, wherein said crests and troughs are spaced in the transverse direction from the bonding sites by a undeformed portion of the respective connector sheet strip.

8. The wearing article defined by claim 7, wherein
   wherein each said connector sheet strip contains thermoplastic polymeric which is molten and solidified at the respective bonding sites where the proximal section of said connector sheet strip is bonded to said one waist region; and
   the undeformed portion of said connector sheet strip is free of said molten and solidified thermoplastic polymer.

9. The wearing article defined by claim 1, wherein said folding guide is free of direct attachment to said one waist region.

10. The wearing article defined by claim 3, wherein said folding guide is spaced in the transverse direction from the bonding sites by a undeformed portion of the respective connector sheet strip.

11. The wearing article defined by claim 10, wherein
   the thermoplastic polymeric of each said connector sheet strip is in a molten and solidified state at the respective bonding sites where the proximal section of said connector sheet strip is bonded to said one waist region; and
   the undeformed portion of each said connector sheet strip is free of both (i) the deformed thermoplastic polymer of the folding guide and (ii) the molten and solidified thermoplastic polymer at the bonding sites.

12. The wearing article defined by claim 10, wherein a thickness of each said connector sheet strip in the undeformed portion thereof is greater than along the associated folding line.

13. A disposable wearing article having a longitudinal direction and a transverse direction orthogonal to each other; said article comprising:
   a front waist region;
   a rear waist region;
   a crotch region;
   each of said regions having a pair of side edges opposed to each other in said transverse direction, and opposite inner and outer surfaces, the inner surface being adapted to face a wearer's skin in use and the outer surface being adapted to face away from the wearer's skin in use; and
   connector sheet strips attached to one of said front and rear waist regions in a vicinity of the associated side edges;
   each of said connector sheet strips respectively comprising:
   a proximal section fixed to the inner surface of said one waist region in the vicinity of one of said associated side edges;
   a flap section moveable between a first position where said flap section extends in the transverse direction inward from said proximal section and a second position where said flap section extends in the transverse direction outward from said proximal section, said flap section having a surface that is opposed to said inner surface of said one waist region when the flap section is in the first position;

a fastening element provided on said surface of said flap section and releasably engageable with the outer surface of the other waist region; and a folding guide between said flap section and said proximal section, said folding guide extending along said proximal section to facilitate unfolding of said flap section from the first position to the second position;

wherein said folding guide comprises multiple alternating crests and troughs.

14. The wearing article defined by claim 13, wherein said proximal section has a flexural rigidity in said transverse direction higher than that of said folding guide; and said flap section also has a flexural rigidity in said transverse direction higher than that of said folding guide.

15. The wearing article defined by claim 14, wherein said folding guide is spaced, in the transverse direction and by a undeformed portion of the respective connector sheet strip, from bonding sites where the respective proximal section is bonded to the respective side edge of said one waist region.

16. The wearing article defined by claim 15, wherein a distance between one of the crests and an adjacent one of the troughs, as measured in a thickness direction of the respective connector sheet strip, is greater than a thickness of the respective connector sheet strip outside said folding guide.

17. The wearing article defined by claim 16, wherein wherein each said connector sheet strip contains thermoplastic polymeric which is molten and solidified at the respective bonding sites where the proximal section of said connector sheet strip is bonded to said one waist region; and the undeformed portion of said connector sheet strip is free of said molten and solidified thermoplastic polymer.

* * * * *